(12) United States Patent
Barlow et al.

(10) Patent No.: US 7,299,095 B1
(45) Date of Patent: Nov. 20, 2007

(54) ELECTRICAL CONTACT ASSEMBLY

(75) Inventors: Anna Barlow, Santa Clarita, CA (US); Christopher Fleck, Marina del Ray, CA (US); Buehl E. Truex, Glendora, CA (US); Edward G. Rourke, Topanga, CA (US)

(73) Assignee: Pacesetter, Inc., Sylmar, CA (US)

( * ) Notice: Subject to any disclaimer, the term of this patent is extended or adjusted under 35 U.S.C. 154(b) by 614 days.

(21) Appl. No.: 10/739,436

(22) Filed: Dec. 17, 2003

(51) Int. Cl.
*A61N 1/00* (2006.01)

(52) U.S. Cl. .......................... 607/37; 607/36
(58) Field of Classification Search ................ 607/36, 607/37; 439/296, 310, 312, 317, 319, 320
See application file for complete search history.

(56) References Cited

U.S. PATENT DOCUMENTS

| | | | |
|---|---|---|---|
| 4,278,093 A | 7/1981 | Lafortune et al. | 128/419 |
| 4,934,366 A * | 6/1990 | Truex et al. | 607/37 |
| 4,961,253 A | 10/1990 | Balsells | 29/173 |
| 5,076,270 A * | 12/1991 | Stutz, Jr. | 607/37 |
| 5,324,311 A * | 6/1994 | Acken | 607/37 |
| 5,413,595 A | 5/1995 | Stutz, Jr. | 607/635 |
| 5,662,692 A | 9/1997 | Paspa et al. | 607/37 |
| 5,730,628 A | 3/1998 | Hawkins | 439/843 |
| 5,769,671 A * | 6/1998 | Lim | 439/843 |
| 5,807,144 A | 9/1998 | Sivard | 439/816 |
| 6,198,969 B1 | 3/2001 | Kuzma | 607/37 |
| 6,430,442 B1 | 8/2002 | Peters et al. | 607/37 |
| 6,895,276 B2 * | 5/2005 | Kast et al. | 607/37 |

FOREIGN PATENT DOCUMENTS

EP 0448651 B1 7/1996
WO WO 03/075414 A1 9/2003

* cited by examiner

*Primary Examiner*—Carl Layno
*Assistant Examiner*—Brian T. Gedeon

(57) ABSTRACT

An electrical contact assembly comprises an annular housing defining an interior space, the housing including a tubular wall having an outer surface facing the interior space and an inner surface defining a central opening adapted to receive an electrical contact, the wall defining at least one aperture. Contained within the interior space of the housing is a garter spring having an inner diameter, the garter spring encircling the outer surface of the wall under preload so that a portion of the inner diameter of the spring projects through the at least one aperture into the central opening of the housing for engaging an electrical contact received within the central opening. An implantable medical device incorporating such an electrical contact assembly is also disclosed.

19 Claims, 7 Drawing Sheets

ELECTRICAL CONTACT ASSEMBLY

FIELD OF THE INVENTION

The present invention relates generally to electrical contacts for establishing electrical connections between circuit elements, and particularly to electrical contact assemblies of the kind using garter spring contact elements.

BACKGROUND

Although it will be evident to those skilled in the art that electrical contact assemblies as described herein have broad applicability in the electrical connector field, the electrical contact assemblies will be described in terms of a specific context, namely, cardiac pacemakers for providing precisely controlled stimulation pulses to the tissue of the heart.

IMDs are in use providing electrical pulses to stimulate body tissue via one or more electrical leads extending between the IMD and the tissue to be stimulated. The leads typically provide bidirectional electrical communication between the IMD's pulse generator and the body tissue, transmitting stimulation pulses to the tissue and sensed electrical signals generated by the tissue to the pulse generator. An example of this type of technology is a pacemaker and a pacing lead which provides electrical stimulation to the heart. The pacemaker is usually implanted in a subcutaneous cavity and the lead or leads extend either transvenously to the internal cavities or chambers of the heart or to patch electrodes affixed to an external surface of the heart.

A pacing lead generally includes at least one electrode on a distal end of the lead and an electrical connector assembly on the proximal end of the lead for connecting the at least one electrode to the pacemaker. Most of today's connector assemblies conform to industry wide standards such as the IS-1 and VS-1 standards. The connector assembly on the proximal end of the lead and the at least one electrode are connected by an electrical conductor extending within an insulated body of the lead. It is common practice for the leads to include two or more electrodes and two or more corresponding electrical contacts on the electrical connector assembly. A typical lead in use today is the bipolar lead carrying a tip electrode and a ring electrode on the distal end of the lead and an in-line electrical connector assembly on the proximal end of the lead. The connector assembly has a pin terminal contact electrically connected to the tip electrode by means of a first coil or cable conductor and a ring terminal contact electrically connected to the ring electrode by a second coil or cable conductor.

The connector assembly is received within a receptacle in a header forming part of the pacemaker. The header is typically made from an epoxy material that is assembled and bonded to the main body of the pacemaker. The main body of the pacemaker is generally a metallic, self-contained, hermetically sealed housing enclosing a battery and electronic circuitry for generating and controlling the timing of the electrical stimuli delivered by the lead.

Electrical contact elements such as toroidal shaped extension springs (usually referred to as garter springs) are mounted within the receptacle of the header to make electrical contact with the pin and ring terminal contacts on the lead connector assembly. Generally, as is the case with garter contacts, the electrical contact elements in the header are passive in that they rely on the deformation of the contact elements under load to maintain contact with the electrical terminal contacts carried by the connector assembly on the lead. Electrical signals must be reliably transferred by these contact elements bidirectionally between the body tissue to be stimulated and the circuitry of the pulse generator. Low electrical resistance contacts are especially important to reliably transfer the low level sensed signals generated by the body tissue. The reliability of the contact system must be maintained under multiple insertion/withdrawals of the lead connector assembly, and the electrical contact element within the pacemaker receptacle must be sufficiently flexible to accept a range of lead sizes so as to accommodate the dimensional tolerances of the connector assembly.

It is further important for the electrical connector assembly on the proximal end of a lead to be securely retained within the receptacle of the pacemaker to prevent inadvertent decoupling. In addition, the insertion and withdrawal forces applied to the electrical connector assembly must be maintained below certain prescribed levels. Preferably, the force required to insert the electrical connector assembly into the pacemaker receptacle should be minimized. There are ISO industry standards governing the maximum allowable insertion force of leads.

It is furthermore important that the electrical contact elements within the pacemaker receptacle not be damaged or pulled out of the receptacle by the connector assembly. Existing garter spring designs in particular have been known to roll or pop out of their retaining grooves or to otherwise become damaged as a result of repeated insertions and withdrawals of connector assembly.

SUMMARY

In accordance with one specific, exemplary embodiment, there is provided an electrical contact assembly comprising a garter spring having an inner diameter and a garter spring retainer. The garter spring retainer comprises a tubular wall receiving the garter spring, the tubular wall having an inner cylindrical surface defining a retainer opening adapted to receive an electrical contact. The tubular wall further includes an outer, cylindrical surface having an outer diameter smaller than the inner diameter of the garter spring in the relaxed state of the spring, the garter spring being thereby preloaded when the garter spring is in place on the tubular wall. The tubular wall further has at least one aperture through which a corresponding section of the garter spring projects inwardly into the retainer opening for engaging the electrical contact received therein.

Pursuant to another specific, exemplary embodiment, there is provided an electrical contact assembly comprising an annular housing defining an interior space, the housing including a tubular wall having an outer surface facing the interior space and an inner surface defining a central opening adapted to receive an electrical contact, the wall defining at least one aperture. Contained within the interior space of the housing is a garter spring having an inner diameter, the garter spring encircling the outer surface of the wall under preload so that a portion of the inner diameter of the spring projects through the at least one aperture into the central opening of the housing for engaging an electrical contact received within the central opening.

Pursuant to another illustrative embodiment, there is provided an implantable medical device for delivering electrical stimuli via a detachable electrical lead having a connector assembly on a proximal end of the lead. The implantable medical device comprises a pulse generator for generating the electrical stimuli, a sealed housing containing the pulse generator and a header affixed to the sealed housing. The header defines at least one receptacle for detachably receiving the connector assembly on the lead, the at least one receptacle containing at least one electrical contact assembly electrically coupled to the pulse generator via a feedthrough carried by the sealed housing. The at least one electrical contact assembly is adapted to be engaged by a contact on the connector assembly. The at least one electrical contact assembly comprises an annular housing defining a central opening for receiving the connector assembly contact, the housing containing a garter spring under preload and having an inner wall defining at least one aperture. A portion of the preloaded garter spring projects through the aperture into the central opening of the annular housing for engaging the contact on the connector assembly.

In accordance with yet another illustrative embodiment, there is provided a system for electrically stimulating body tissue, the system comprising an implantable lead and an implantable medical device. The implantable lead comprises a distal end carrying at least one electrode adapted to engage the tissue to be stimulated, and a proximal end carrying a connector assembly including a contact electrically connected to the at least one electrode. The implantable medical device comprises a pulse generator for generating electrical stimuli, a sealed housing containing the pulse generator, and a header affixed to the sealed housing. The header defines at least one receptacle for detachably receiving the connector assembly on the lead, the at least one receptacle containing at least one electrical contact assembly electrically coupled to the pulse generator via a feedthrough carried by the sealed housing. The at least one electrical contact assembly is adapted to be engaged by the contact on the connector assembly and comprises an annular housing defining a central opening for receiving the connector assembly contact. The housing contains a garter spring under preload and has an inner wall defining at least one aperture. A portion of the preloaded garter spring projects through the aperture into the central opening of the annular housing for engaging the contact on the connector assembly.

BRIEF DESCRIPTION OF THE DRAWINGS

The foregoing and other objects, features and advantages of the electrical contact assembly will be evident to those skilled in the art from the detailed description below, taken together with the accompanying drawings, in which.

DETAILED DESCRIPTION OF THE ILLUSTRATIVE EMBODIMENTS

The following description is of a best mode presently contemplated for the electrical contact assembly. This description is not to be taken in a limiting sense but is made merely for the purpose of describing the general principles of the electrical contact assembly. The scope of the invention should be ascertained with reference to the accompanying claims. In the description that follows, like numerals or reference designators are used to refer to like parts or elements throughout. Moreover, the context in which the electrical contact assembly is principally shown and described herein, namely, the electrical connection between the terminals within a pacemaker receptacle and the contacts on the electrical connector assembly on the proximal end of an associated lead forming part of a body tissue electrical stimulation and sensing system, is illustrative only; it will be understood by those skilled in the art that the electrical contact assembly has broader applicability in the electrical connector field.

Figure 1:
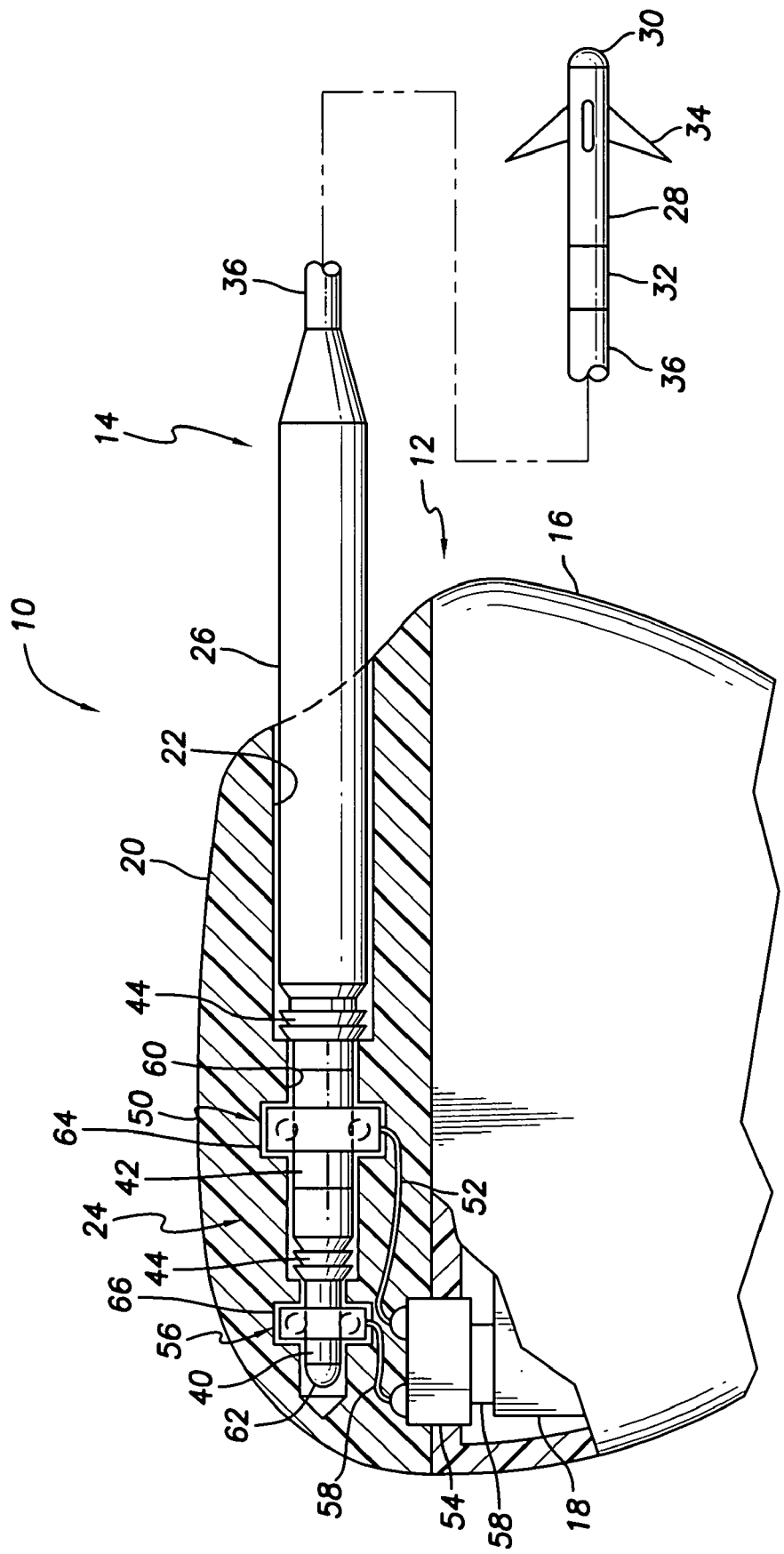
FIG. 1 is a side elevation view, partly in cross section, of a portion of a tissue stimulation system including an IMD incorporating a specific, exemplary embodiment of the electrical contact assembly.

FIG. 1 shows a system 10 for electrically stimulating selected body tissue. The system 10 incorporates a specific, exemplary embodiment of the electrical contact assembly and in essence comprises an IMD 12 that may take the form of a pacemaker and an associated electrical lead 14 that may comprise a bipolar pacing lead.

The IMD 10 comprises a pulse generator that includes a hermetically sealed metallic housing 16 containing a power supply (typically a battery) and electronic circuitry 18 and an attached header 20 having at least one receptacle 22 for receiving an in-line electrical connector assembly 24 attached to a proximal end 26 of the bipolar pacing lead 14. The header 20 may be either integral with the housing 16 or formed as a separate element and attached to the housing. Generally, when the header 20 is formed as a separate element as illustrated in FIG. 1, it is molded from epoxy material. Although the header 20 is shown for simplicity as a single molded piece, in practice the header or a portion thereof, such as a sleeve, defining the receptacle(s) will typically be made of a plurality of appropriately joined, individually molded parts.

The bipolar pacing lead 14 comprises a distal end 28 carrying a tip electrode 30, a ring electrode 32 proximal of the tip electrode and a plurality of tines 34 extending outwardly from an insulating lead body 36 between the electrodes 30 and 32 for anchoring the distal end 28 of the lead within a chamber of the heart or within the coronary sinus region of the heart, all as well known in the art. The in-line electrical connector assembly 24 includes a pin contact 40 electrically connected to the tip electrode 30 and a ring contact 42 electrically connected to the ring electrode 32. These connections are implemented by means of coil or cable conductors (not shown) enclosed within the lead body 36. The connector assembly 24 further comprises sets of seals 44 for preventing the entry of body fluids into the receptacle 22. When the connector assembly 24 is fully inserted into the receptacle (as shown in FIG. 1), an electrical connection is established between the ring contact 42 on the connector assembly and a first electrical contact assembly 50 carried by the header 20. The first electrical contact assembly 50 is in turn connected to the electronic circuitry 18 contained within the pacemaker housing by wires 52 and a feedthrough 54. Similarly, when the connector assembly 24 is inserted into the receptacle, electrical communication is established between the pin contact 40 and the circuitry 18 by way of a second electrical contact assembly 56, wires 58 and the feedthrough 54. The receptacle 22 has a stepped configuration, comprising a larger bore 60 for receiving the portion of the connector assembly carrying the ring contact 42 and a smaller diameter bore 62 for receiving the pin contact 40.

The first electrical contact assembly 50 is captured within an annular channel 64 formed in the wall of the larger bore 60 of the receptacle 22. It will be seen that although the first electrical contact assembly 50 is able to float to some extent within the annular channel 64, the walls of the channel prevent axial movement of the first contact assembly 50 beyond the confines of the channel 64. A similar channel 66 formed in the wall of the smaller bore 62 retains the second contact assembly 56 in similar fashion. The annular channels 64 and 66 thus constrain the first and second electrical contact assemblies 50 and 56 from being pulled out of the receptacle 22 when the connector assembly 24 is withdrawn, or from being pushed further into the receptacle when the connector assembly is inserted.

With reference now to FIGS. 2-6, there is shown a first, specific, exemplary embodiment of the first electrical contact assembly 50. Except for its size, the second electrical contact assembly 56 (FIG. 1) is identical to the first assembly 50; accordingly, only the first assembly will be described in detail.

Figure 3:
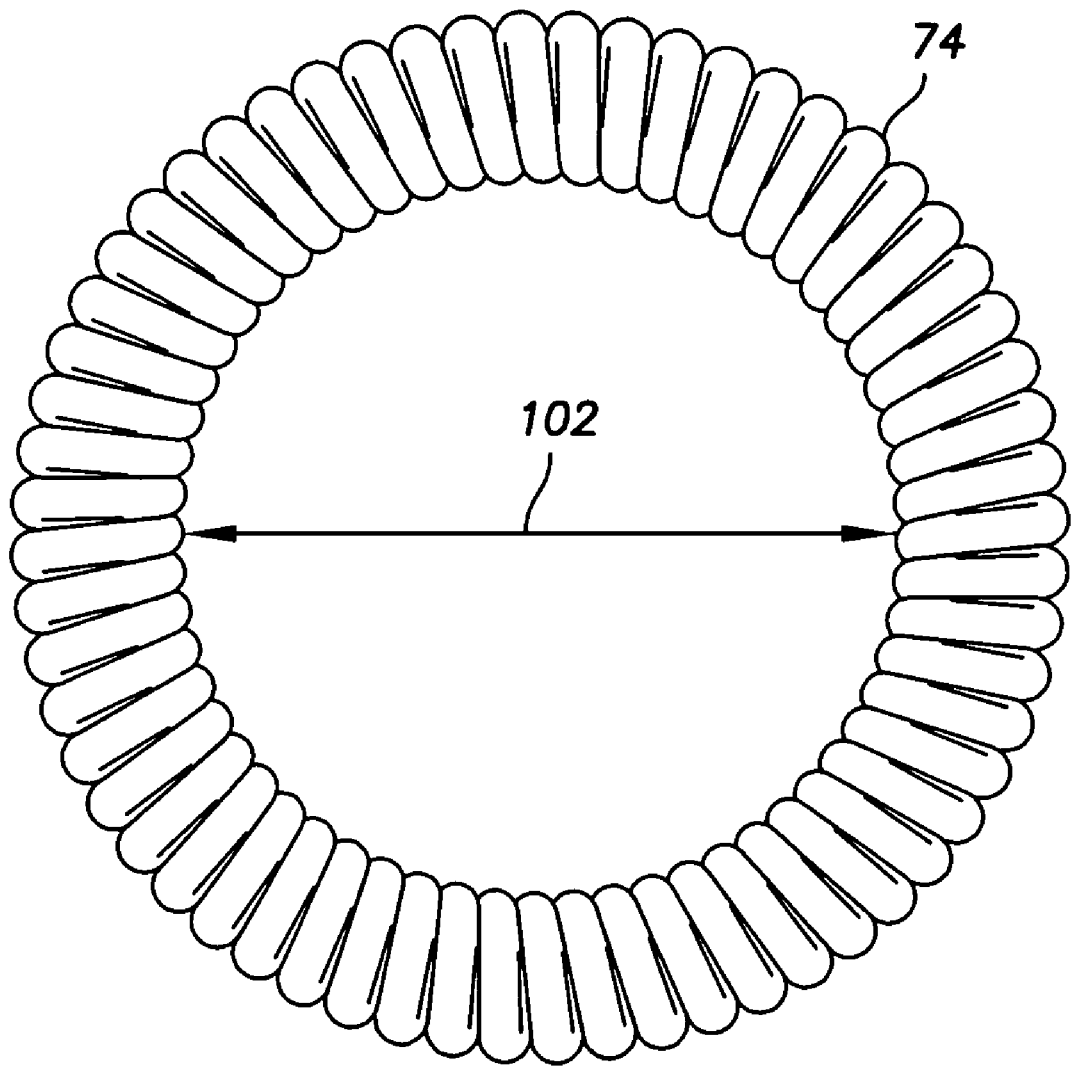
FIG. 3 is a front elevation view of a garter spring that may be used in an electrical contact assembly, the garter spring being shown in its relaxed state.

The first contact assembly 50 generally comprises an annular housing 70 defining an interior annular space 72 containing a garter spring 74. The housing 70 is basically a two-part structure, comprising a garter spring retainer 76 and a cap 78 received by the retainer 76. The garter spring 74, shown in its relaxed state in FIG. 3, is constructed in accordance with teachings well known in the art. Accordingly, the garter spring 74 may comprise an extension spring that has been curved into a ring or annular shape with the ends of the extension spring bonded together, for example, by laser welding. The spring 74 is preferably made of a biocompatible, biostable, electrically conductive material such as MP35N alloy. Suitable garter spring contact elements may be obtained commercially from Bal Seal Engineering, Inc., Foothill Ranch, Calif., U.S.A.

The garter spring retainer 76 comprises a generally tubular wall 80 having axially spaced ends 82 and 84. The tubular wall 80 has an outer cylindrical surface 86 that faces the interior space 72 within the housing 70 and receives the garter spring 74. The tubular wall 80 has an inner cylindrical surface 88 that defines a central opening 90 for receiving the ring contact 42 (FIG. 1) on the electrical connector assembly 24.

Formed in the tubular wall 80 of the retainer 76 are three circumferentially spaced apertures 92, 94 and 96, each preferably in the form of a circumferentially-extending slot. Although three such slots spaced apart equiangularly about the circumference of the tubular wall are shown in the drawings, more or less than three may be employed. The retainer 76 further includes a flange 98 extending radially outwardly from the end 84 of the tubular wall 80. The flange 98 includes an outer, chamfered edge 100.

Figure 2:
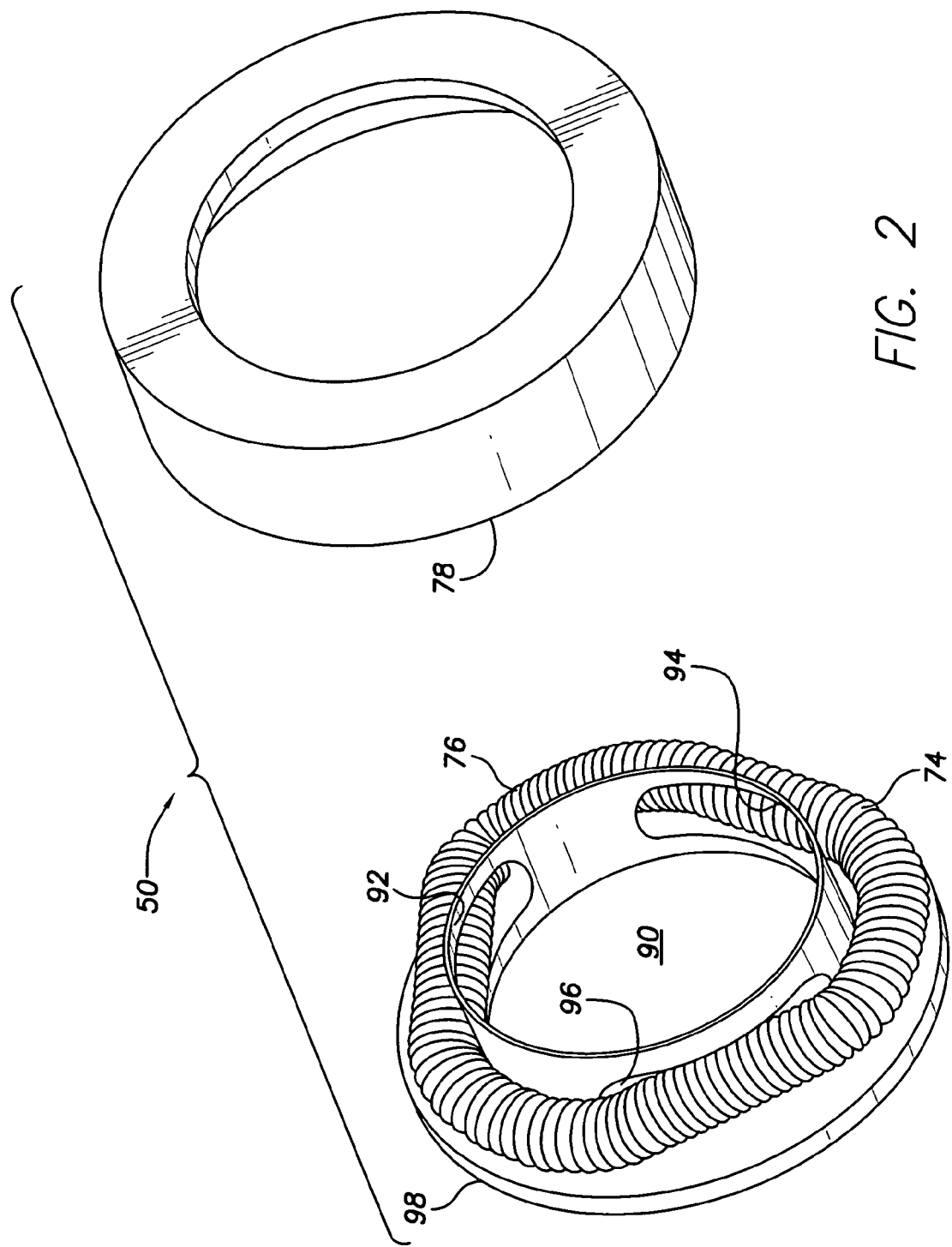
FIG. 2 is an exploded, perspective view of an electrical contact assembly in accordance with one specific, exemplary embodiment.
Figure 5:
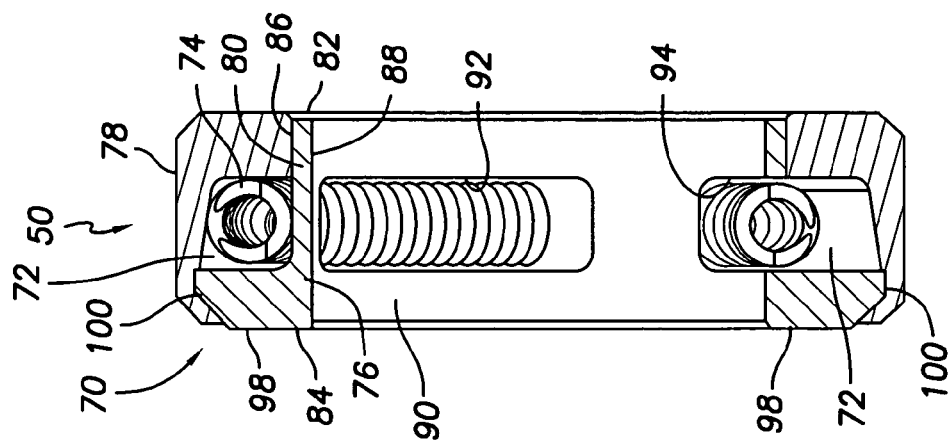
FIG. 5 is a side elevation view, in cross section, of the electrical contact assembly of FIG. 4 as seen along the line 5-5 in FIG. 4.
Figure 4:
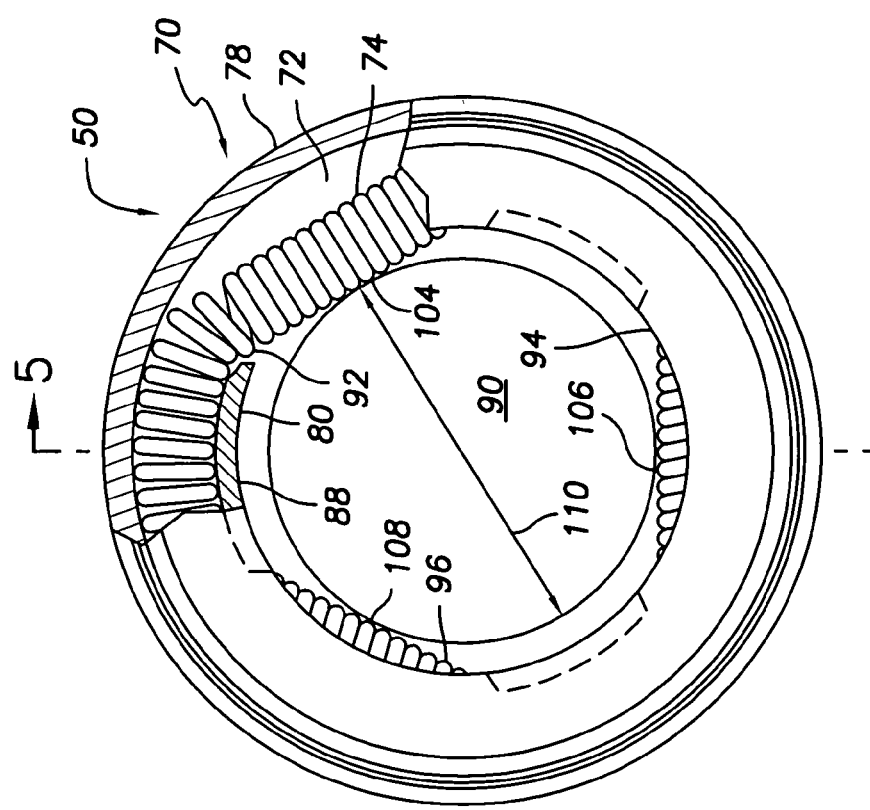
FIG. 4 is a rear elevation view, partly in cross section, of the electrical contact assembly of FIG. 2, in its assembled state.

In its relaxed state, the garter spring 74 has an inside diameter 102 (FIG. 3) that is smaller than the diameter of the outer surface 86 of the tubular wall 80 receiving the spring. By way of non-limiting example, the inside diameter 102 of the garter spring 74 in its relaxed state may be 0.095 inch (2.41 mm) while the diameter of the spring-receiving surface 86 may be 0.146 inch (3.71 mm). Accordingly, as best seen in FIGS. 2, 4 and 5, when the garter spring 74 is mounted on the tubular wall 80 so as to encircle the wall, the spring is extended and thus under a preload. As a result, the inside diameter of the spring projects through the slots 92, 94 and 96 of the tubular wall 80 and into the central opening 90 of the housing to define three contact regions 104, 106 and 108. The inwardly projecting contact regions 104, 106 and 108 define a diameter 110 (FIG. 4) slightly smaller than the diameter of the ring contact 42 on the connector assembly of the lead. By way of example only, for a ring contact diameter of 0.126 inch (3.2 mm), the contact region diameter 110 may be 0.116 inch (2.95 mm). Accordingly, with three slots in the tubular wall 80, three sections of the garter spring project into the interior of the retainer defining as many electrical contact regions between the garter spring 74 and the ring electrode 42. It will appreciated that the dimensions of the tubular wall 80 and the geometry and spring characteristics of the garter spring 74 can be selected to precisely control the insertion force of the connector assembly so as to assure reliable, multipoint electrical contact.

Installation of the cap 78 on the spring retainer 76 completes the electrical contact assembly 50. The cap 78 is an annular structure with a generally L-shaped cross section as best seen in FIGS. 2 and 5-7. More specifically, the cap 78 comprises a radially extending annular disk 116 having an inside diameter slightly larger than the outside diameter of the tubular wall 80 and a rearwardly extending tubular end 118 whose inside diameter mates with the outer edge 100 of the flange 98. A rear extremity 120 of the tubular end 118 is swaged over the chamfered edge 100 of the flange 98 completing the assembly with the garter spring 74 captured between the cap 78, the flange 98 and the outer surface 86 of the tubular wall 80.

Figure 6:
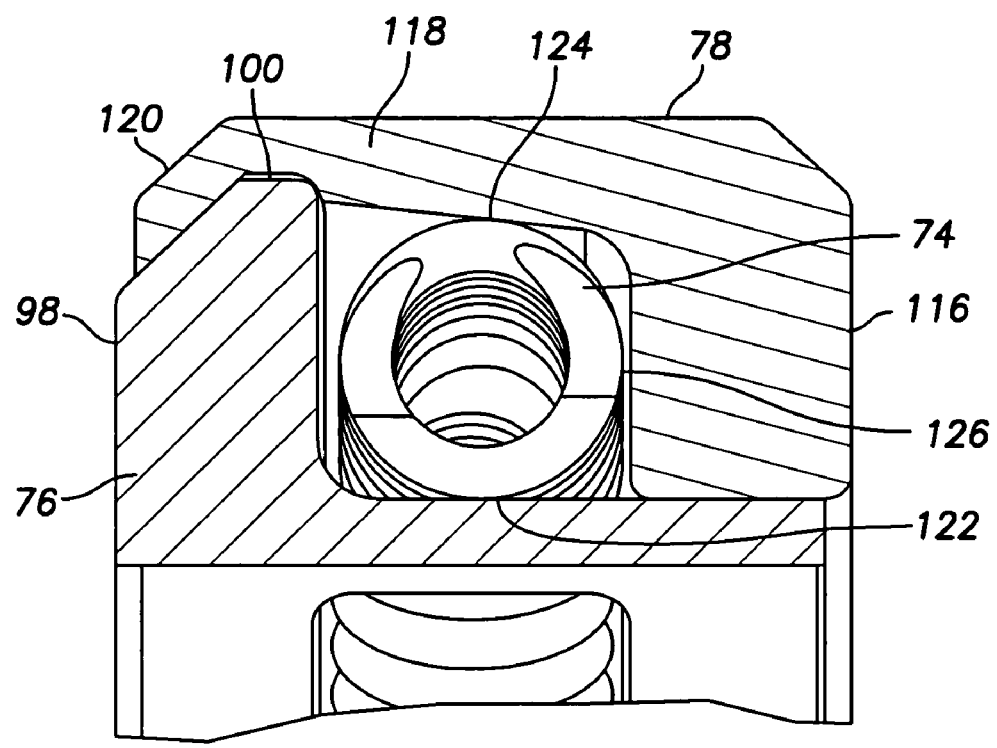
FIG. 6 is an enlargement of a portion of the side elevation view of FIG. 5.
Figure 7:
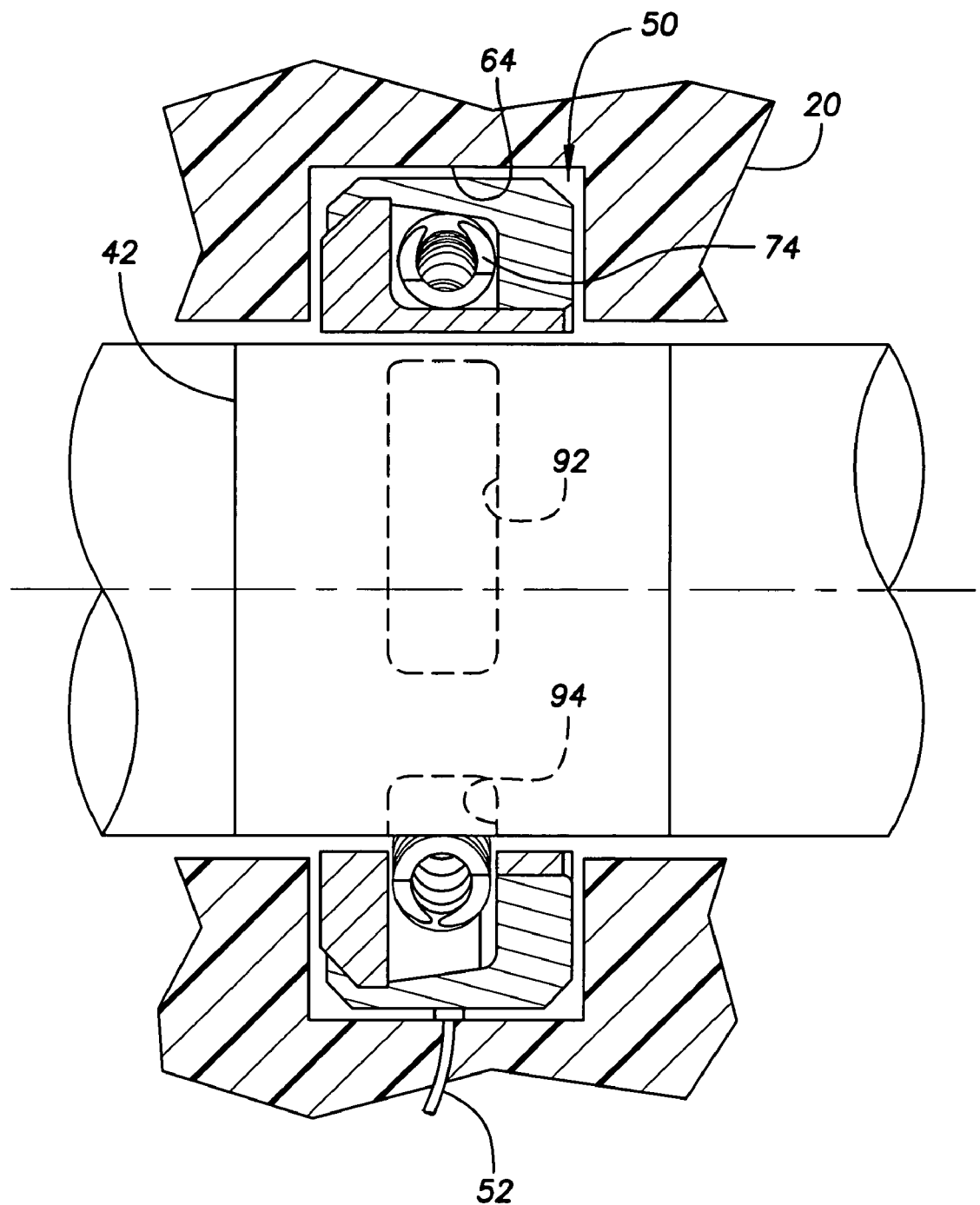
FIG. 7 is enlarged side elevation view, partly in cross section, of a portion of the IMD shown in FIG. 1.

FIG. 6 illustrates the multipoint contact between the garter spring 74 on the one hand and the retainer 76 and cap 78 on the other. For example, in the specific embodiment shown, the garter spring is in electrical contact with the retainer 76 at point 122, and with the cap at points 124 and 126. Reliable and secure electrical continuity is thereby established from the ring contact 42 on the connector assembly 24 through the garter spring 74, the contact assembly housing 70 and the wire 52 that is welded to the outer surface of the housing cap (FIG. 7).

Figure 8:
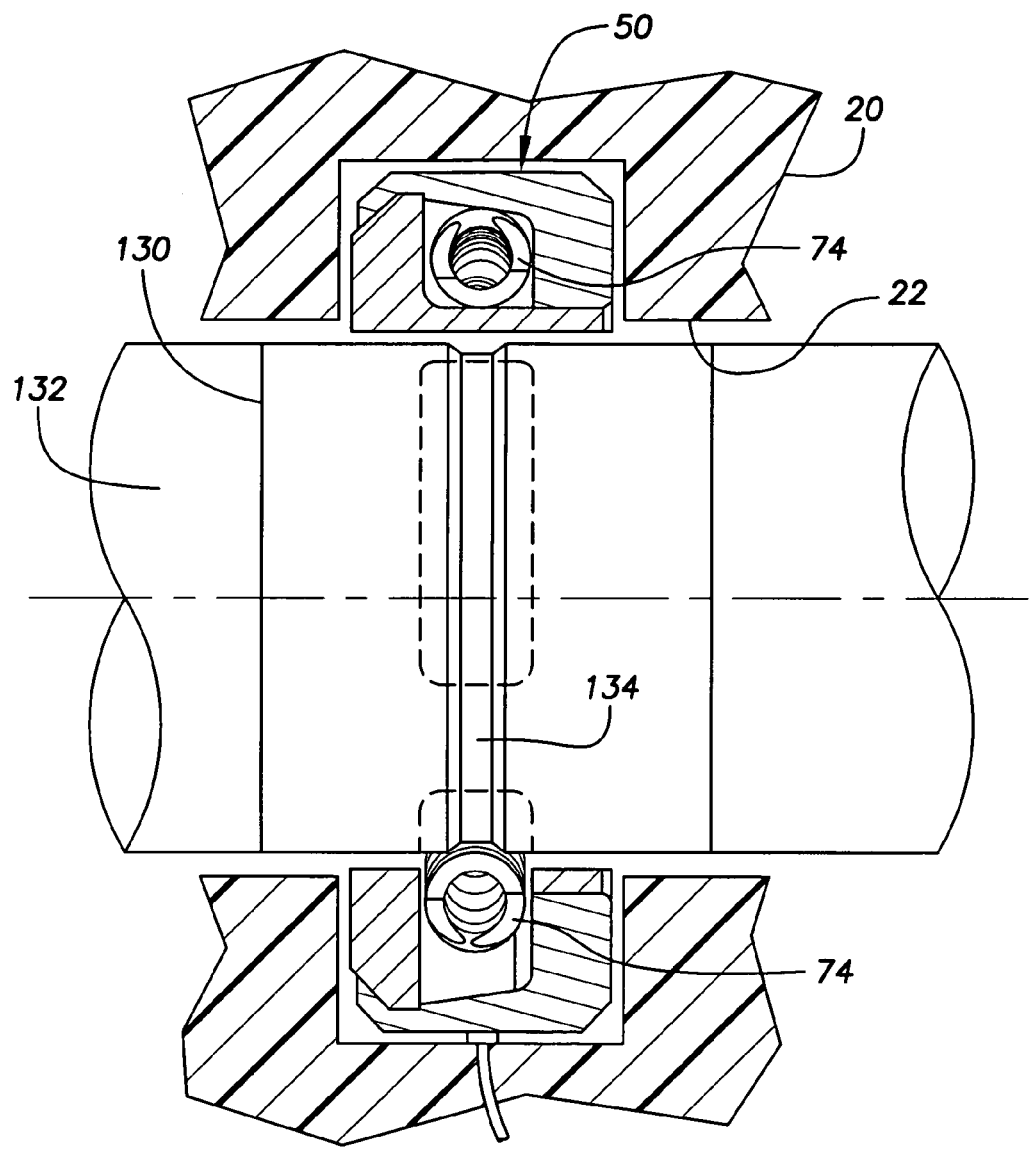
FIG. 8 is a side elevation view, in cross section, similar to that shown in FIG. 7, illustrating a specific, exemplary alternative embodiment of the electrical contact assembly.

With reference to FIG. 8, there is shown an alternative embodiment of the electrical contact assembly in which a ring contact 130 on a lead connector assembly 132 has an annular groove 134 about its outer circumference. The portions of the garter spring 74 extending into the opening 90 of the retainer snap into the groove 134 when the electrical connector assembly 132 is fully inserted so as to releasably latch the connector assembly in place within the receptacle 22.

The foregoing description directed to the first contact assembly is equally applicable to the second contact assembly and to any additional contact assemblies that may be used in association with an electrical connector assembly on a multipolar lead.

The various embodiments of the electrical contact assembly described herein have a number of advantages. For example, with the garter spring 74 securely contained within the housing 70 except for the sections of the spring projecting into the central opening 90, the spring is not subject to damage or being pushed or pulled out of the header 20 as a result of insertion or withdrawal of the connector assembly 24. The contact assembly retains its electrical signal transfer reliability under multiple insertion/withdrawals of the lead connector assembly, maintains continuous contact even when the lead connector assembly is wiggled, does not contribute excess force to insertion/withdrawal forces and provides a low electrical resistance thus assuring a reliable conductive path for both high and low voltages. It will also be appreciated that the reliability of the electrical contact assembly is due in part to preloading of the garter spring 74 causing a predetermined radial load to be applied to the ring contact on the connector assembly. The cap and other elements of the electrical contact assembly can be designed so that when the ring contact is received within the contact assembly, the garter spring will press against the interior wall of the cap to provide an additional radially inwardly directed load further assuring the reliability of the electrical contact. The contact assembly can accept a range of contact diameters thereby accommodating the tolerances of the connector assembly contact. The contact assembly is compatible with various industry standards, including the IS-1 standard and the new IS-4 standard.

While illustrative embodiments of the electrical contact assembly have been shown and described, numerous variations and alternative embodiments will occur to those skilled in the art. Such variations and alternative embodiments are contemplated, and can be made without departing from the spirit and scope of the invention as defined in the appended claims.

What is claimed is:

1. An electrical contact assembly for an implantable medical device, the electrical contact assembly comprising:
   a garter spring having an inner diameter, the garter spring being a coiled spring; and
   a garter spring retainer comprising a tubular wall receiving said garter spring, the tubular wall having an inner cylindrical surface defining a retainer opening adapted to receive an electrical contact of an implantable lead, said tubular wall further including an outer cylindrical surface having an outer diameter larger than the inner diameter of the garter spring in the relaxed state of the spring, the garter spring being thereby extended and preloaded when the garter spring is in place on the outer cylindrical surface of the tubular wall, the tubular wall further having at least one aperture through which a corresponding section of the garter spring projects inwardly into the retainer opening for engaging the electrical contact of the implantable lead received therein.

2. The electrical contact assembly of claim 1 wherein:
   said at least one aperture comprises at least one slot extending circumferentially about said tubular wall of the retainer.

3. The electrical contact assembly of claim 2 wherein:
   the tubular wall of the retainer has a plurality of slots spaced apart circumferentially about said tubular wall.

4. The electrical contact assembly of claim 3 wherein:
   said plurality of slots are of equal length.

5. The electrical contact assembly of claim 4 wherein:
   the plurality of slots are equiangularly spaced about said tubular wall.

6. The electrical contact assembly of claim 5 wherein:
   the tubular wall defines three slots.

7. The electrical contact assembly of claim 1 wherein:
   the retainer includes a flange projecting radially outward from one end of the tubular portion.

8. The electrical contact assembly of claim 7 wherein:
   the assembly includes a cylindrical cap engaging an outer edge of the flange, the garter spring being captured between the flange and the cap.

9. The electrical contact assembly of claim 8 wherein:
   the garter spring engages the retainer and cap at multiple contact points.

10. An electrical contact assembly for an implantable medical device, the electrical contact assembly comprising:
    an annular housing defining an interior space, the housing including a tubular wall having an outer surface facing said interior space and an inner surface defining a central opening adapted to receive an electrical contact of an implantable lead, said wall defining at least one aperture; and
    a garter spring contained within the interior space of the housing, the garter spring having an inner diameter, the outer surface of the tubular wall having an outer diameter larger than the inner diameter of the garter spring in the relaxed state of the spring, the garter spring encircling the outer surface of said wall and being extended and preloaded so that a portion of said inner diameter of the spring projects through said at least one aperture into the central opening of the housing for engaging the electrical contact of the implantable lead received within said central opening;
    wherein the garter spring is a coiled spring.

11. The electrical contact assembly of claim 10 wherein:
    said at least one aperture comprises at least one slot extending circumferentially along said wall of said housing.

12. The electrical contact assembly of claim 11 wherein:
    the wall defines a plurality of circumferentially spaced-apart slots.

13. The electrical contact assembly of claim 12 wherein:
    said plurality of slots are of equal length.

14. The electrical contact assembly of claim 13 wherein:
    the plurality of slots are equiangularly spaced apart.

15. The electrical contact assembly of claim 10 wherein:
    the wall of the housing defines three slots.

16. An implantable medical device for delivering electrical stimuli via a detachable electrical lead having a connector assembly on a proximal end of the lead, the implantable medical device comprising:
    a pulse generator for generating said electrical stimuli;
    a sealed housing containing said pulse generator; and
    a header affixed to said sealed housing, said header defining at least one receptacle for detachably receiving the connector assembly on the lead, said at least one receptacle containing at least one electrical contact assembly electrically coupled to said pulse generator via a feedthrough carried by the sealed housing, the at least one electrical contact assembly being adapted to be engaged by a contact on the connector assembly, the at least one electrical contact assembly comprising an annular housing defining a central opening for receiving the connector assembly contact, the housing containing a garter spring, the garter spring being a coiled spring, the annular housing having a tubular wall, the tubular wall having an inner cylindrical surface defining a retainer opening adapted to receive the contact on the connector assembly, the tubular wall having an outer cylindrical surface with an outer diameter larger than the inner diameter of the garter spring in a relaxed state of the spring, the garter spring being thereby extended and preloaded when the garter spring is in place on the outer cylindrical surface of the tubular wall, a portion of said preloaded garter spring projecting through said aperture into the central opening of the annular housing for engaging the contact on the connector assembly.

17. The implantable medical device of claim 16 wherein:
the receptacle is defined by a wall having an annular channel for receiving the at least one electrical contact assembly.

18. A system for electrically stimulating body tissue comprising:
   a. an implantable lead comprising:
      a distal end carrying at least one electrode adapted to engage the tissue to be stimulated, and a proximal end carrying a connector assembly including a contact electrically connected to said at least one electrode; and
   b. an implantable medical device comprising:
      a pulse generator for generating electrical stimuli;
      a sealed housing containing said pulse generator; and
      a header affixed to said sealed housing, said header defining at least one receptacle for detachably receiving the connector assembly on the lead, said at least one receptacle containing at least one electrical contact assembly electrically coupled to said pulse generator via a feedthrough carried by the sealed housing, the at least one electrical contact assembly being adapted to be engaged by the contact on the connector assembly, the at least one electrical contact assembly comprising an annular housing defining a central opening for receiving the connector assembly contact, the housing containing a garter spring, the garter spring being a coiled spring, the annular housing having a tubular wall, the tubular wall having an inner cylindrical surface defining a retainer opening adapted to receive the contact on the connector assembly, the tubular wall having an outer cylindrical surface with an outer diameter larger than the inner diameter of the garter spring in a relaxed state of the spring, the garter spring being thereby extended and preloaded when the garter spring is in place on the outer cylindrical surface of the tubular wall, a portion of said preloaded garter spring projecting through said aperture into the central opening of the annular housing for engaging the contact on the connector assembly.

19. The system of claim 18 wherein:
the contact on the connector assembly has a groove formed therein for receiving the projecting portion of said garter spring for detachably latching the connector assembly in said receptacle.

* * * * *